US008017614B2

(12) United States Patent
Shook et al.

(10) Patent No.: US 8,017,614 B2
(45) Date of Patent: Sep. 13, 2011

(54) ARYLINDENOPYRIMIDINES COMPOUND AND USE AS AN ADENOSINE A2A RECEPTOR ANTAGONISTS

(75) Inventors: Brian C. Shook, Gilbertsville, PA (US); Paul F. Jackson, New Hope, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 389 days.

(21) Appl. No.: 12/253,358

(22) Filed: Oct. 17, 2008

(65) Prior Publication Data

US 2009/0111827 A1    Apr. 30, 2009

Related U.S. Application Data

(60) Provisional application No. 60/982,247, filed on Oct. 24, 2007.

(51) Int. Cl.
*A61K 31/497* (2006.01)
*A61K 31/505* (2006.01)
*A01N 43/54* (2006.01)
*C07D 239/70* (2006.01)
*C07D 403/00* (2006.01)

(52) U.S. Cl. .................. 514/252.16; 514/267; 544/249; 544/359

(58) Field of Classification Search .............. 514/252.16, 514/267; 544/249, 359
See application file for complete search history.

(56) References Cited

U.S. PATENT DOCUMENTS
2004/0127510 A1    7/2004 Heintzelman et al.

FOREIGN PATENT DOCUMENTS
WO    WO 2005/042500 A1    5/2005

OTHER PUBLICATIONS

Vippagunta SR, Brittain HG, and Grant D J, "Crystalline solids," Advanced Drug Delivery Reviews, May 2001,48(1), 3-26.*
Asherio, A., et al. "Prospective Study of Caffeine Consumption and Risk of Parkinson's Disease in Men and Women", Ann. Neurol 2001:50:56-63.
Chen, J-F. et al. "Neuroprotective by Caffeine and $A_{2a}$ Adenosine Receptor Inactivation in a Model of Parkinson's Disease", Journal of Neuroscience, 2001, vol. 21, RC143.
Diamond, I., et al. "The Critical Role of Adenosine A2a Receptors and Gi βγ Subunits in Alcoholism and Addiction: From Cell Biology to Behavior", Cell Biology of Addiction, (2006), pp. 291-316.
Ferre, S., et al. "Stimulation of High-Affinity Adenosine $A_2$ Receptors Decreases the Affinity of Dopamine $D_2$ Receptors in Rat Strital Membranes", Proc. Natl. Acad. Sci, USA, vol. 88, p. 7328-7241 (1991).
Fink, J., et al. "Molecular Cloning of the Rat $A_2$ Adenosine Receptor: Selective Co-Expression with $D_2$ Dopamine Receptors in Rat Striaatum", Molecular Brain Reserch, 14 (1992), pp. 186-195.
Gessi, S., et al. "$A_{2A}$ Adenosine Receptors in Human Peripheral Blood Cells", British Journal of Pharmacology (2000), 129, pp. 2-11.
Hack, P., et al. "Adaptations in Adenosine Signaling in Drug Dependence: Therapeutic Implications", Critical Review in Neurobiology, vol. 15 (2003) pp. 235-274.
Impagnatiello, F., et al. "Adenosine Receptors in Neurological Disorders", Emerging Therapeutic Targets (2000), pp. 635-664.
Ikeda, K., et al. "Neuroprotection by Adenosine $A_{2A}$ Receptor Blockade in Experimental Models of Parkinson's Disease", Journal of Neurochemistry (2002), 80, p. 262-270.
Mally, J., et al. "Efficacy of an Adenosine Antagonist, Theophylline, in Essential Tremor: Comparison with Placebo and Propanolol", Journal of the Neurological Sciences 132 (1995), pp. 129-132.
Matasi, J., et al. "The Discovery and Synthesis of Novel Adenosine Receptor ($A_{2A}$) Antagonists", Bioorganic &n Medicinal Chemistry Letters 15 (2005), pp. 1333-1336.
Rosin, D., et al. "Immunohistochemical Localization of Adenosine $A_{2A}$ Receptors in the Rat Central Nervous System", Journal of Comparative Neurology 401:163-186 (1998).
Salim, H., et al. "Activation of Adenosine $A_1$ and $A_{2A}$ Receptors Modulates Dopamine $D_2$ Receptor-Induced Responses in Stably Transfected Human Neuroblalstoma Cells", Journal of Neurochemistry, 74, 432-439 (2000).
Stiles, G., et al. "Adenosine Receptors", Journal of Biological Chemistry, vol. 267, No. 10, pp. 6451-6454 (1992).
Thorsell, A., et al., Effect of the Adenosine A2A Receptor Antagaonist 3,7-Dimethyl-Propargylxanthine on Anxiety-like and Depression-Like Behavior and Alcohol Consumption in Wistar Rats, Alcoholism: Clinical and Experimental Research, vol. 31,No. 8 Aug. 2007, pp. 1302-1307.
Yacoubi, M., et al. "Adenosine $A_{2A}$ Receptors and Depression", Neurology (Suppl. 6), 2003:61 pp. S82-S87.
Chen, W., et al. "A Colorimetric Assay for Measuring Activation of $G_s$-$G_q$-Coupled Signaling Pathways", Analytical Biochemistry 226, (1995), pp. 349-354.
Comings, D, et al. "Multivariate Analysis of Associations of 42 Genes in ADHD, ODD and Conduct Disorder", Clin. Genetics 58 (2000), pp. 31-40.
Domenici, M., et al. "Behavioral and Electrophysiological Effects of the Adenosine $A_{2A}$ Receptor Antagonist SCH 58261 in R6/2 Huntington's Disease Mice", Neurobiology of Disease 28 (2007), pp. 197-205.

* cited by examiner

*Primary Examiner* — San-Ming Hui
*Assistant Examiner* — Paul Zarek
(74) *Attorney, Agent, or Firm* — Peter L. Herridge

(57) ABSTRACT

This invention relates to a novel arylindenopyrimidine, A, and its therapeutic and prophylactic uses. Disorders treated and/or prevented include Parkinson's Disease.

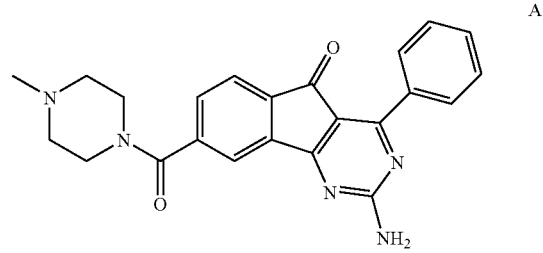

10 Claims, No Drawings

ARYLINDENOPYRIMIDINES COMPOUND AND USE AS AN ADENOSINE A2A RECEPTOR ANTAGONISTS

CROSS REFERENCE TO RELATED APPLICATIONS

This application claims priority of the benefits of the filing of U.S. Provisional Application Ser. No. 60/982,247, filed Oct. 24, 2007. The complete disclosures of the aforementioned related U.S. patent application is/are hereby incorporated herein by reference for all purposes.

FIELD OF THE INVENTION

This invention relates to a novel arylindenopyrimidine and its therapeutic and prophylactic uses. Disorders treated and/or prevented include neurodegenerative and movement disorders ameliorated by antagonizing Adenosine A2a receptors.

BACKGROUND OF THE INVENTION

Adenosine A2a Receptors Adenosine is a purine nucleotide produced by all metabolically active cells within the body. Adenosine exerts its effects via four subtypes of cell surface receptors (A1, A2a, A2b and A3), which belong to the G protein coupled receptor superfamily (Stiles, G. L. Journal of Biological Chemistry, 1992, 267, 6451). A1 and AS couple to inhibitory G protein, while A2a and A2b couple to stimulatory G protein. A2a receptors are mainly found in the brain, both in neurons and glial cells (highest level in the striatum and nucleus accumbens, moderate to high level in olfactory tubercle, hypothalamus, and hippocampus etc. regions) (Rosin, D. L.; Robeva, A.; Woodard, R. L.; Guyenet, P. G.; Linden, J. Journal of Comparative Neurology, 1998, 401, 163).

In peripheral tissues, A2a receptors are found in platelets, neutrophils, vascular smooth muscle and endothelium (Gessi, S.; Varani, K.; Merighi, S.; Ongini, E.; Bores, P. A. British Journal of Pharmacology, 2000, 129, 2). The striatum is the main brain region for the regulation of motor activity, particularly through its innervation from dopaminergic neurons originating in the substantial nigra. The striatum is the major target of the dopaminergic neuron degeneration in patients with Parkinson's Disease (PD). Within the striatum, A2a receptors are co-localized with dopamine D2 receptors, suggesting an important site for the integration of adenosine and dopamine signaling in the brain (Fink, J. S.; Weaver, D. Ri; Rivkees, S. A.; Peterfreund, R. A.; Pollack, A. E.; Adler, E. M.; Reppert, S. M. Brain Research Molecular Brain Research, 1992, 14, 186).

Neurochemicat studies have shown that activation of A2a receptors reduces the binding affinity of D2 agonist to their receptors. This D2R and A2aR receptor-receptorinteraction has been demonstrated instriatal membrane preparations of rats (Ferre, S.; con Euler, G.; Johansson, B.; Fredholm, B. B.; Fuxe, K. Proceedings of the National Academy of Sciences I of the United States of America, 1991, 88, 7238) as well as in fibroblast cell lines after transfected with A2aR and D2R cDNAs (Salim, H.; Ferre, S.; Dalal, A.; Peterfreund, R. A.; Fuxe, K.; Vincent, J. D.; Lledo, P. M. Journal of Neurochemistry, 2000, 74, 432). In viva, pharmacological blockade of A2a receptors using A2a antagonist leads to beneficial effects in dopaminergic neurotoxin MPTP (1-methyl-4-pheny-1,2,3, 6-tetrahydropyridine)-induced PC) in various species, including mice, rats, and monkeys (Ikeda, K.; Kurokawa, M.; Aoyana, S.; Kuwana, Y. Journal of Neurochemistry, 2002, 80, 262).

Furthermore, A2a knockout mice with genetic blockade of A2a function have been found to be less sensitive to motor impairment and neurochemical changes when they were exposed to neurotoxir MPTP (Chen, J. F.; Xu, K.; I Petzer, J. P.; Steal, R.; Xu, Y. H.; Beilstein, M.; Sonsalla, P. K.; Castagnoli, K.; Castagnoli, N., Jr.; Schwarsschild, M. A. Journal of Neuroscience, 2001, 1 21, RC1 43).

In humans, the adenosine receptor antagonist theophylline has been found to produce beneficial effects in PD patients (Mally, J.; Stone, T. W. Journal of the Neurological Sciences, 1995, 132, 129). Consistently, recent epidemiological study has shown that high caffeine consumption makes people less likely to develop PD (Ascherio, A.; Zhang, S. M.; Heman, M. A.; Kawachi, I.; Colditz, G. A.; Speizer, F. E.; Willett, W. C. Annals of Neurology, 2001, 50, 56). In summary, adenosine A2a receptor blockers may provide a new class of antiparkinsonian agents (Impagnatiello, F.; Bastia, E.; Ongini, E.; Monopoli, A. Emerging Therapeutic Targets, 2000, 4, 635).

Antagonists of the $A_{2A}$ receptor are potentially useful therapies for the treatment of addiction. Major drugs of abuse (opiates, cocaine, ethanol, and the like) either directly or indirectly modulate dopamine signaling in neurons particularly those found in the nucleus accumbens, which contain high levels of $A_{2A}$ adenosine receptors. Dependence has been shown to be augmented by the adenosine signaling pathway, and it has been shown that administration of an $A_{2A}$ receptor antagonist redues the craving for addictive substances ("The Critical Role of Adenosine $A_{2A}$ Receptors and Gi βγ Subunits in Alcoholism and Addiction: From Cell Biology to Behavior", by Ivan Diamond and Lina Yao, (The Cell Biology of Addiction, 2006, pp 291-316) and "Adaptations in Adenosine Signaling in Drug Dependence: Therapeutic Implications", by Stephen P. Hack and Macdonald J. Christie, Critical Review in Neurobiology, Vol. 15, 235-274 (2003)). See also Alcoholism: Clinical and Experimental Research (2007), 31(8), 1302-1307.

An $A_{2A}$ receptor antagonist could be used to treat attention deficit hyperactivity disorder (ADHD) since caffeine (a non selective adenosine antagonist) can be useful for treating ADHD, and there are many interactions between dopamine and adenosine neurons. Clinical Genetics (2000), 58(1), 31-40 and references therein.

Antagonists of the $A_{2A}$ receptor are potentially useful therapies for the treatment of depression. $A_{2A}$ antagonists are known to induce activity in various models of depression including the forced swim and tail suspension tests. The positive response is mediated by dopaminergic transmission and is caused by a prolongation of escape-directed behavior rather than by a motor stimulant effect. Neurology (2003), 61(suppl 6) S82-S87.

Antagonists of the $A_{2A}$ receptor are potentially useful therapies for the treatment of anxiety. $A_{2A}$ antagonist have been shown to prevent emotional/anxious responses in vivo. Neurobiology of Disease (2007), 28(2) 197-205.

SUMMARY OF THE INVENTION

Compound A is a potent small molecule antagonist of the Adenosine A2a receptor.

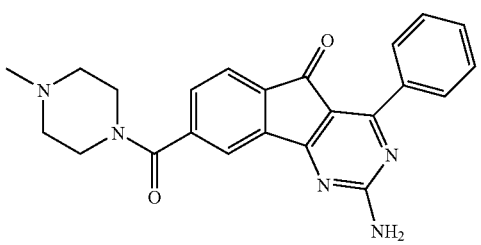

DETAILED DESCRIPTION OF THE INVENTION

The invention provides a compound A.

A and solvates, hydrates, tautomers, and pharmaceutically acceptable slats thereof.

This invention further provides a method of treating a subject having a condition ameliorated by antagonizing Adenosine A2a receptors, which comprises administering to the subject a therapeutically effective dose of the instant pharmaceutical composition.

This invention further provides a method of preventing a disorder ameliorated by antagonizing Adenosine A2a receptors in a subject, comprising of administering to the subject a prophylactically effective dose of the compound of claim 1 either preceding or subsequent to an event anticipated to cause a disorder ameliorated by antagonizing Adenosine A2a receptors in the subject.

The instant compounds can be isolated and used as free bases. They can also be isolated and used as pharmaceutically acceptable salts.

Examples of such salts include hydrobromic, hydroiodic, hydrochloric, perchloric, sulfuric, maleic, fumaric, malic, tartaric, citric, adipic, benzoic, mandelic, methanesulfonic, hydroethanesulfonic, benzenesulfonic, oxalic, palmoic, 2 naphthalenesulfonic, p-toluenesulfonic, cyclohexanesulfamic and saccharic.

This invention also provides a pharmaceutical composition comprising the instant compound and a pharmaceutically acceptable carrier.

Pharmaceutically acceptable carriers are well known to those skilled in the art and include, but are not limited to, from about 0.01 to about 0.1 M and preferably 0.05 M phosphate buyer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by antagonizing Adenosine A2a receptors, which comprises administering to the subject a therapeutically effective dose of the instant pharmaceutical composition.

In one embodiment, the disorder is a neurodegenerative or movement disorder. Examples of disorders treatable by the instant pharmaceutical composition include, without limitation, Parkinson's Disease, Huntington's Disease, Multiple System Atrophy, Corticobasal Degeneration, Alzheimer's Disease, and Senile Dementia.

In one preferred embodiment, the disorder is Parkinson's disease.

As used herein, the term "subject" includes, without limitation, any animal or artificially modified animal having a disorder ameliorated by antagonizing adenosine A2a receptors. In a preferred embodiment, the subject is a human.

Administering the instant pharmaceutical composition can be effected or performed using any of the various methods known to those skilled in the art. The instant compounds can be administered, for example, intravenously, intramuscularly, orally and subcutaneously. In the preferred embodiment, the instant pharmaceutical composition is administered orally. Additionally, administration can comprise giving the subject a plurality of dosages over a suitable period of time. Such administration regimens can be determined according to routine methods.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.001 mg/kg of body weight to about 200 mg/kg of body weight of the instant pharmaceutical composition. In another embodiment, the therapeutically and/or prophylactically effective dose is a dose sufficient to deliver from about 0.05 mg/kg of body weight to about 50 mg/kg of body weight. More specifically, in one embodiment, oral doses range from about 0.05 mg/kg to about 100 mg/kg daily. In another embodiment, oral doses range from about 0.05 mg/kg to about 50 mg/kg daily, and in a further embodiment, from about 0.05 mg/kg to about 20 mg/kg daily. In yet another embodiment, infusion doses range from about 1.0, ug/kg/min to about 10 mg/kg/min of inhibitor, admixed with a pharmaceutical carrier over a period ranging from about several minutes to about several days. In a further embodiment, for topical administration, the instant compound can be combined with a pharmaceutical carrier at a drug/carrier ratio of from about 0.001 to about 0.1.

The invention also provides a method of treating addiction in a mammal, comprising administering a therapeutically effective dose of the compound of Formula A.

The invention also provides a method of treating ADHD in a mammal, comprising administering a therapeutically effective dose of the compound of Formula A.

The invention also provides a method of treating depression in a mammal, comprising administering a therapeutically effective dose of the compound of Formula A.

The invention also provides a method of treating anxiety in a mammal, comprising administering a therapeutically effective dose of the compound of Formula A.

EXAMPLES

Compound A can be prepared by methods known to those who are skilled in the art. The following reaction schemes are only meant to represent examples of the invention and are in no way meant to limit the invention.

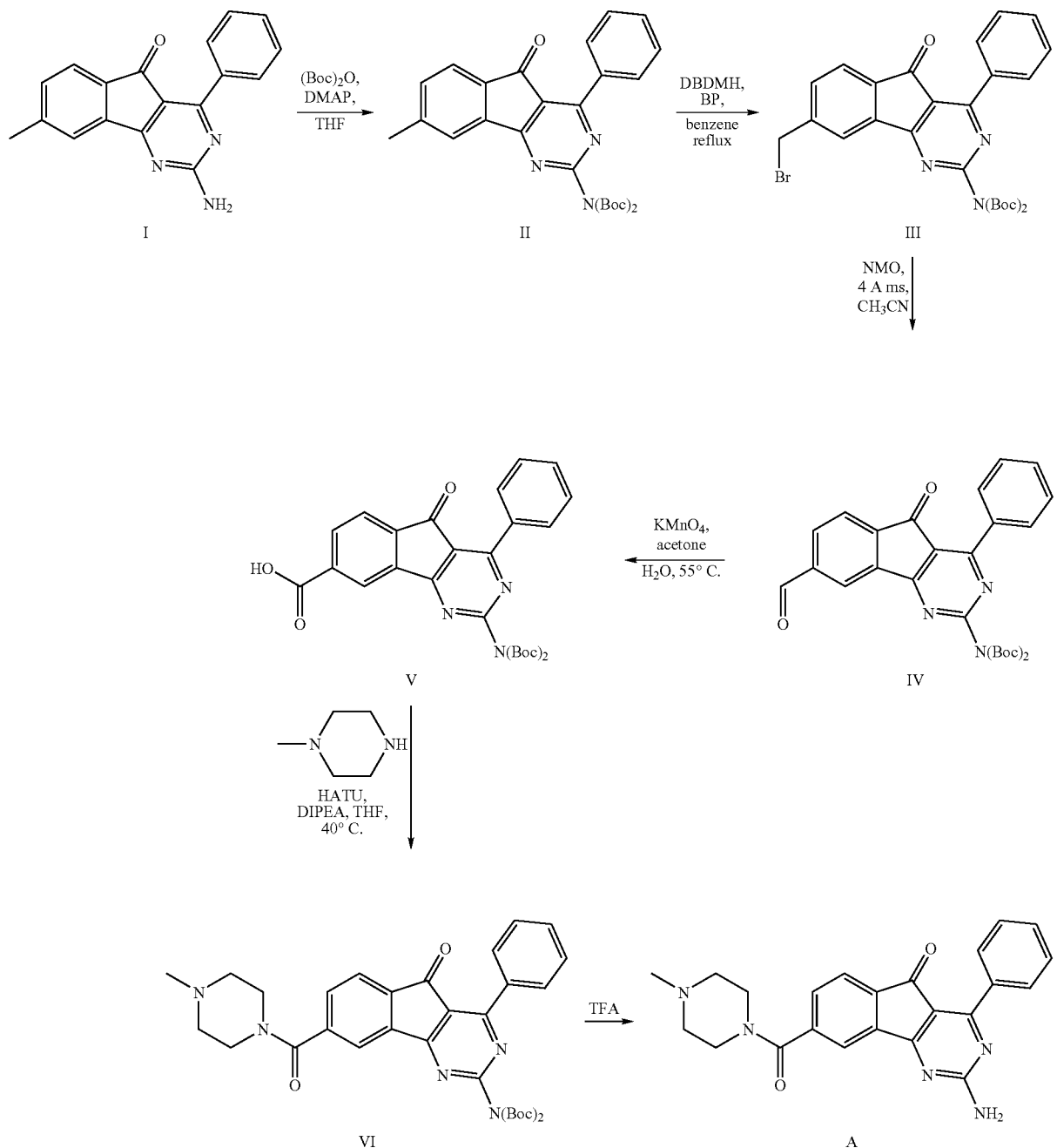

Compound A can be prepared by methods known to those who are skilled in the art. The following reaction schemes are only meant to represent examples of the invention and are in no way meant to be a limit of the invention.

Scheme 1 illustrates the synthetic route leading to compound A. Starting amino pyrimidine I and following the path indicated by the arrows, protection of the amino (NH$_2$) can be accomplished using di-tert-butyl dicarbonate ((Boc)$_2$O) in tetrahydrofuran (THF) in the presence of dimethylamino pyridine (DMAP). The resulting di-Boc protected II can undergo a radical initiated benzylic bromination using 1,3-dibromo-5,5-dimethylhydantoin (DBDMH) and benzoyl peroxide (BP) in benzene at reflux to give the corresponding benzyl bromide III. Benzyl bromide III can then be oxidized to the corresponding aldehyde IV using 4-methylmorpholine N-oxide (NMO) and 4 Å molecular sieves (ms) in acetonitrile (CH$_3$CN). The resulting aldehyde IV can be further oxidized to the corresponding carboxylic acid V using potassium permanganate (KMnO$_4$) in an acetone/water mixture at 55° C. The carboxylic acid V can then be converted to the corresponding amide VI using 1-methylpiperazine, O-(7-Azabenzotriazol-1-yl)-N,N,N',N'-tetramethyluronium hexafluorophosphate (HATU), and diisopropylethyl amine (DIPEA) in THF at 40° C. Finally, the amide VI can be deprotected using trifluoroacetic acid (TFA) to give compound A.

Example A

Step a (II): Neat dimethylamino pyridine (850 mg, 7.0 mmol) was added to a THF solution (300 mL) of I (20.0 g, 69.7 mmol) and (Boc)$_2$O (38.0 g, 174.2 mmol). After 2 h the mixture was diluted with ethyl acetate (EtOAc) and then washed with water and brine, dried (Na$_2$SO$_4$) and concentrated. The resulting solid was suspended in EtOAc (250 mL) and filtered. The solid was washed with EtOAc (2×100 mL) then dried in vacuo to give 25.6 g of II.

Example A

Step b (III): II (25.6 g, 52.6 mmol) was completely dissolved in benzene (200 mL) by warming then dibromodimethyl hydantoin (8.3 g, 28.9 mmol) and benzoyl peroxide (1.0 g, 4.2 mmol) were added sequentially. The mixture was heated to reflux for 16 h. The solution was then cooled to rt, diluted with EtOAc and then washed with saturated aqueous NaHCO$_3$, water and brine. The solution was dried (Na$_2$SO$_4$), concentrated and purified via column chromatography (5-20% EtOAc/heptane). First chromatography afforded 6 g of III that contained ~10% II and a second chromatography gave an additional 12 g of III containing 10% II.

Example A

Step c (IV): Solid N-methyl morpholine N-oxide (2.5 g, 21.2 mmol) was added to a CH$_3$CN (300 mL) of III (6.0 g, 10.6 mmol) and 4 Å ms (10.5 g). After 18 h at rt the mixture was filtered and the filtrate was diluted with EtOAc and washed with water and brine, dried (Na$_2$SO$_4$), and chromatographed to give 3.6 g of IV.

Example A

Step d (V): Solid KMnO$_4$ was added to an acetone/water solution (100 mL/25 mL) of IV (3.6 g, 7.2 mmol) and the resulting mixture was heated to 55° C. After 14 h the mixture was cooled to rt and filtered. The filtrate was diluted with EtOAc and washed with water and brine, dried (Na$_2$SO$_4$), concentrated and purified by column chromatography to give 2.1 g of V.

Example A

Step e (VI): Neat piperazine (0.4 mL, 3.6 mmol) was added to a THF solution (60 mL) of acid V (1.7 g, 3.3 mmol), diisopropylethylamine (1.7 mL, 9.9 mmol), and HATU (1.3 g, 3.3 mmol). The resulting mixture was heated to 40° C. After 18 h the mixture was concentrated and purified via column chromatography to give 1.8 g of amide VI.

Example A

Step f

2-Amino-8-(4-methyl-piperazine-1-carbonyl)-4-phenyl-indeno[1,2-d]pyrimidin-5-one

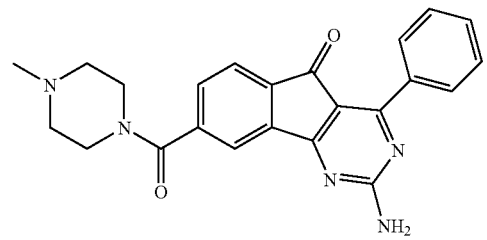

JNJ-39928122

(A): The amide VI was then stirred in 25 ML CH$_2$Cl$_2$/TFA (4:1). After 3 h the mixture was concentrated, neutralized with saturated aqueous NaHCO$_3$ and filtered to give 1 g of crude A. The solid was purified via column chromatography to give 893 mg of as the free base, which was dissolved in THF and added to 10 mL of 1 N HCl in ether, concentrated, and dried in vacuo to give (A) as the di-HCl salt. $^1$H NMR (400 MHz, CHLOROFORM-d) δ ppm 2.34 (s, 3H), 2.39 (br. s., 2H), 2.52 (d, J=2.20 Hz, 2H), 3.46 (br. s, 2H), 3.84 (br. s, 2H), 5.86 (br. s, 2H), 7.46-7.64 (m, 4H), 7.78 (d, J=7.58 Hz, 1H), 7.85 (s, 1H), 8.07 (dd, J=7.83, 1.71 Hz, 2H); MS m/e 400 (M+H).

Biological Assays and Activity Ligand Binding Assay for Adenosine A2a Receptor

Ligand binding assay of adenosine A2a receptor was performed using plasma membrane of HEK293 cells containing human A2a adenosine receptor (PerkinElmer, RB-HA2a) and radioligand [3H] CGS21680 (PerkinElmer, NET1021). Assay was set up in 96-well polypropylene plate in total volume of 200, uL by sequentially adding 20 pL1:20 diluted membrane, pLassay buffer (50 mM Tris HCl, pH7.4 10 mM MgCl2, 1 mM EDTA) containing [3H] CGS2168O, 50, uL diluted compound (4×) or vehicle control in assay buffer. Nonspecific binding was determined by 80 mM NECA. Reaction was carried out at room temperature for 2 hours before filtering through 96 well GF/C filter plate pre-soaked in 50 mM Tris HCl, pH7.4 containing 0.3% polyethylenimine. Plates were then washed 5 times with cold 50 mM Tris HCl, pH7.4, dried and sealed at the bottom. Microscintillation fluid 30, ul was added to each well and the top sealed. Plates were counted on Packard Topcount for [3H]. Data was analyzed in Microsoft Excel and GraphPad Prism programs. (Varani, K.; Gessi, S.; Dalpiaz, A.; Borea, P. A. British Journal of Pharmacology, 1996, 117, 1693) Adenosine A2a Receptor Functional Assay CHO-K1 cells overexpressing human adenosine A2a receptors and containing cAMP-inducible beta-galactosidase reporter gene were seeded at 40-50 K/well into 96-well tissue culture plates and cultured for two days. On assay day, cells were washed once with 200 pL assay medium (F-12 nutrient mixture/0.1% BSA). For agonist assay, adenosine A2a receptor agonist NECA was subsequently added and cell incubated at 37° C., 5% CO2 for 5 hrs before stopping reaction. In the case of antagonist assay, cells were incubated with antagonists for 5 minutes at R.T. followed by addition of 50 nM NECA. Cells were then incubated at 37° C., 5% CO2 for 5 hrs before stopping experiments by washing cells with PBS twice. 50, uL 1× Tysis buffer (Promega, 5× stock solution, needs to be diluted to 1× before use) was added to each well and plates frozen at −20° C. For, B-galactosidase enzyme calorimetric assay, plates were thawed out at room temperature and 50, uL 2× assay buffer (Promega) added to each well. Color was allowed to develop at 37° C. for 1 h or until reasonable signal appeared. Reaction was then stopped with 150 AL 1 M sodium carbonate. Plates were counted at 405 nm on Vmax Machine (Molecular Devices). Data was analyzed in Microsoft Excel and GraphPad Prism programs. (Chen, W. B.; Shields, T. S.; Cone, R. D. Analytical Biochemistry, 1995, 226, 349; Stiles, G. Journal of Biological Chemistry, 1992, 267, 6451); Haloperidol-induced catalepsy study in C57b1/6 mice Mature male C57b1/6 mice (9-12 week old from ACE) were housed two per cage in a rodent room. Room temperature was maintained at 64-79 degrees and humidity at 30-70% and room lighting at 12 hrs lighV12 hrs dark cycle. On the study day, mice were transferred to the study room. The mice were injected subcutaneously with haloperidol (Sigma H1512, 1.0 mg/ml made in 0.3% tartaric acid, then diluted to 0.2 mg/ml with saline) or vehicle at 1.5 mg/kg, 7.5 ml/kg. The mice were then placed in their home cages with access to water and food. 30 minutes later, the mice were orally dosed with vehicle (0.3% Tween 80 in saline) or compounds at 10 mg/kg, 10 ml/kg (compounds, 1 mg/ml, made in 0.3% Tween 80 in saline, sonicated to obtain a uniform suspension). The mice were then placed in their home cages with access to water and food. 1 hour after oral dose, the catalepsy test was performed. A vertical metal-wire grid (1.0 cm squares) was used for the test.

The mice were placed on the grid and given a few seconds to settle down and their immobility time was recorded until the mice moved their back paw(s). The mice were removed gently from the grid and put back on the grid and their immobility time was counted again. The measurement was repeated three times. The average of three measurements was used for data analysis.

| A2a ASSAY DATA | | |
|---|---|---|
| Compound | $A_2a$ cell-based functional Ki | $A_1$ cell-based functional Ki |
| A | 8.2 nM | 58.4 nM |

AMES Assay Conditions

The purpose of this study was to assess, in vitro, the ability of compounds of the present invention to induce reverse-point mutations in bacteria when treated in the presence and absence of a microsomal activation system.

Compounds were tested in a bacterial/microsomal activation plate incorporation assay using *Salmonella typhimurium* strains TA98, TA100, TA1535, TA1537, and *Escherichia coli* strain $WP_2uvrA$. This study included tests in the absence (buffer) and presence of metabolic activation by an Aroclor® 1254-induced rat liver microsomal preparation (S9 mix). Compounds were tested in all strains under both metabolic conditions at doses of 5, 10, 25, 50, 100, 250, 500, 1000, 2500, and 5000 μg per plate. Mutations were detected by phenotypic reversion to amino acid prototrophy (histidine or tryptophan for *S. typhimurium* or *E. coli* respectively). A test article would be considered positive (mutagenic), if it induces a dose dependent increase in revertant frequency to at least 2-fold that observed in the appropriate concurrent vehicle control (3-fold for TA1535 and TA1537). In addition, the response should be reproducible. Toxicity was detected by a dose dependent decrease in colony counts and/or reduced/absent bacterial lawns. Vehicle treated plates served as the standards for comparison for both mutation and toxicity. Positive control plates were used to assure the functionality of the test system.

Acceptable negative control and positive indicator results were obtained for all strains in the absence and the presence of S9 mix. This assured that the test system was functioning and responsive.

AMES Assay Results

The following results demostrate the desirable AMES-negative quality for the three compounds of the present invention. Not all of the compounds tested in the assay were found to be AMES-negative. For comparison, two similar molecules are shown which possess the undesirable AMES-positive quality. For this assay, AMES-negative is considered to be a desirable quality.

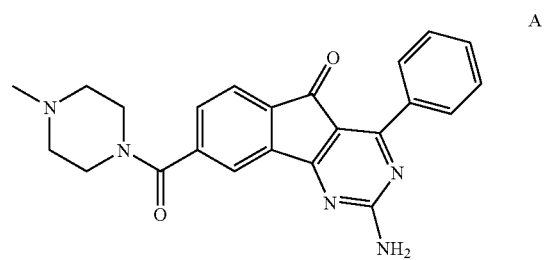

AMES NEGATIVE

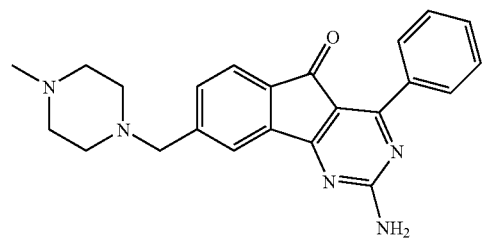

-continued

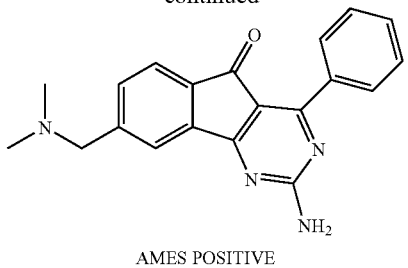

AMES POSITIVE

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

We claim:

1. A compound, which is:

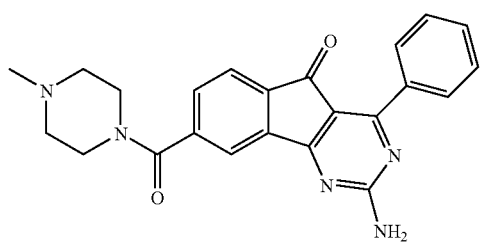

A and pharmaceutically acceptable salts thereof.

2. A pharmaceutical composition comprising the compound of claim 1, and a pharmaceutically acceptable carrier.

3. A method of treating a subject having a disorder ameliorated by antagonizing Adenosine A2a receptors, selected from the group consisting of; Parkinson's Disease, Huntington's Disease, Alzheimer's Disease, Senile Dementia, Addiction, ADHD, Major Depressive Disorder and anxiety, which comprises administering to the subject a therapeutically effective dose of the compound of claim 1.

4. The method of claim 3, comprising administering to the subject a therapeutically effective dose of the pharmaceutical composition of claim 2.

5. The method of claim 3, wherein the disorder is selected from the group consisting of Parkinson's Disease, Huntington's Disease, Alzheimer's Disease, and Senile Dementia.

6. The method of claim 3, wherein the disorder is Parkinson's Disease.

7. The method of claim 3, wherein the disorder is addiction.

8. The method of claim 3, wherein the disorder is ADHD.

9. The method of claim 3, wherein the disorder is Major Depressive Disorder.

10. The method of claim 3, wherein the disorder is anxiety.

* * * * *